US012016849B2

(12) United States Patent
Nelson et al.

(10) Patent No.: US 12,016,849 B2
(45) Date of Patent: Jun. 25, 2024

(54) MAGNESIUM PICOLINATE COMPOSITIONS AND METHODS OF USE

(71) Applicant: Bonafide Health, LLC, Harrison, NY (US)

(72) Inventors: Deanna J. Nelson, Raleigh, NC (US); James R. Komorowski, Trumbull, CT (US)

(73) Assignee: Bonafide Health, LLC, Harrison, NY (US)

( * ) Notice: Subject to any disclaimer, the term of this patent is extended or adjusted under 35 U.S.C. 154(b) by 0 days.

(21) Appl. No.: 15/730,694

(22) Filed: Oct. 11, 2017

(65) Prior Publication Data
US 2018/0098976 A1 Apr. 12, 2018

Related U.S. Application Data

(60) Provisional application No. 62/407,362, filed on Oct. 12, 2016.

(51) Int. Cl.
*A61K 31/4402* (2006.01)
*A61K 9/28* (2006.01)
*A61K 33/06* (2006.01)

(52) U.S. Cl.
CPC ............ *A61K 31/4402* (2013.01); *A61K 9/28* (2013.01); *A61K 33/06* (2013.01); *A61K 9/2846* (2013.01)

(58) Field of Classification Search
CPC ......... A61K 9/28; A61K 33/06; A61K 9/0053
See application file for complete search history.

(56) References Cited

U.S. PATENT DOCUMENTS

| | | | | |
|---|---|---|---|---|
| 4,315,927 A | * | 2/1982 | Evans | A23K 20/30 426/74 |
| 6,486,318 B1 | * | 11/2002 | Kumar | C07D 213/79 546/5 |
| 6,582,722 B1 | | 6/2003 | Clark et al. | |
| 8,445,020 B2 | * | 5/2013 | Brandon | A61K 45/06 514/546 |
| 2003/0108624 A1 | | 6/2003 | Kosbab | |
| 2003/0228347 A1 | * | 12/2003 | Clark | A21D 2/145 424/439 |
| 2007/0190209 A1 | | 8/2007 | Sinnott | |
| 2011/0091548 A1 | | 4/2011 | Joanny | |
| 2012/0157533 A1 | | 6/2012 | Liu et al. | |
| 2014/0056976 A1 | * | 2/2014 | Pronovost | A61K 45/06 424/617 |
| 2015/0335599 A1 | | 11/2015 | Brandon et al. | |
| 2016/0235822 A1 | | 8/2016 | Holstein et al. | |
| 2017/0189447 A1 | | 7/2017 | Morris | |
| 2018/0021353 A1 | | 1/2018 | Rathmacher et al. | |
| 2018/0098976 A1 | | 4/2018 | Nelson et al. | |
| 2018/0280333 A1 | | 10/2018 | Beaudoin et al. | |

FOREIGN PATENT DOCUMENTS

| | | |
|---|---|---|
| CN | 102098921 | 6/2011 |
| JP | H05-505935 | 9/1993 |
| JP | H07-145317 | 6/1995 |
| JP | 2010-522216 | 7/2010 |
| JP | 2013-500933 | 1/2013 |
| WO | WO-91/11117 | 8/1991 |
| WO | WO-2009/143072 | 11/2009 |
| WO | WO-2011/015859 | 2/2011 |
| WO | WO-2017/182885 | 10/2017 |

OTHER PUBLICATIONS

De Baaij, J.H.F. et al. "Magnesium in Man: Implications for Health and Disease" Physiol Rev 95: 1-46, 2015 (Year: 2015).*
Crea et al., "Speciation of phytate ion in aqueous solution. Sequestration of magnesium and calcium by phytate at different temperatures and ionic strengths, in $NaCl_{aq}$," Biophysical Chemistry, 2006; 124: pp. 18-26.
Ghosh et al., "Synthesis, characterization and study of antioxidant activity of quercetin-magnesium complex," Spectrochimica Acta Part A: Molecular and Biomolecular Spectroscopy, 2015; 151: pp. 807-813.
Lewandowski et al., "Spectroscopic (Raman, FT-IR and NMR) and theoretical study of alkali metal picolinates," J. Phys. Org. Chem. 2005; 18: pp. 918-928.
Metal Chelates; Table of Stability Constants, [online], [retrieved Sep. 2018]. Retrieved from the Internet: <URL: https://www.dojindo.com/Images/Product%20Photo/Chelate_Table_of_Stability_Constants.pdf>.
Reid et al., "Magnesium-dependent ATPase Activity and Cooperativity of Magnesium Chelatase from *Synechocystis* sp. PCC6803," The Journal of Biological Chemistry, 2004; 279(26): pp. 26893-26899.
Torre et al., "Effects of dietary fiber and phytic acid on mineral availability," Critical Reviews in Food Science & Nutrition, 1991; 30(1): pp. 1-22.
Torreggiani et al., "Copper (II)-Quercetin complexes in aqueous solutions: spectroscopic and kinetic properties," Journal of Molecular Structure, 2005; 744-747: pp. 759-766.
Turnlund et al., "A stable isotope study of copper absorption I young men: effect of phytate and α-cellulose[1-3]," The American Journal of Clinical Nutrition, 1985; 42: pp. 18-23.
Walter et al., "Enhanced selectivity for Mg2+ with a phosphinate-based chelate: APDAP versus APTRA," Dalton Transactions, The Royal Society of Chemistry, 2018; 47: pp. 1879-1887.
Deloume et al., "Structure du picolate de magnésium dihydraté," Acta Crystallogr, Section B, Struct. Crystallogr Cryst. Chem., 29(4): 668-676 (1973). (English abstract included).
International Search Report and Written Opinion for PCT/US2017/056228, dated Dec. 22, 2017.

(Continued)

*Primary Examiner* — Andrew S Rosenthal
(74) *Attorney, Agent, or Firm* — Arnall Golden Gregory LLP

(57) ABSTRACT

The present application relates to magnesium picolinate compositions and methods of use. The methods and compositions disclosed herein are particularly useful for providing bioavailable magnesium to mammals and treating or preventing symptoms of magnesium deficiency.

15 Claims, 10 Drawing Sheets

(56) References Cited

OTHER PUBLICATIONS

Swiderski, et al., "Experimental (FT-IR, FT-Raman, 1H NMR) and theoretical study of magnesium, calcium, strontium, and barium picolinates," Spectrochim. Acta Part A, 2006; 64(1): pp. 24-33.
U.S. Department of Health & Human Services, Food & Drug Administration, "Guidance for Industry: Q3C Impurities: Residual Solvents," Dec. 1997, [online]. Retrieved from the Internet: <URL: https://www.fda.gov/downloads/drugs/guidances/ucm073394.pdf>.
U.S. Department of Health & Human Services, Food & Drug Administration, "Guidance for Industry: Q3D Elemental Impurities," Sep. 2015, [online]. Retrieved from the Internet: <URL: https://www.fda.gov/downloads/drugs/guidances/ucm371025.pdf>.
U.S. Department of Health & Human Services, Food & Drug Administration, "Guidance for Industry: Quality Systems Approach to Pharmaceutical CGMP Regulations," Sep. 2006, [online]. Retrieved from the Internet: <URL: https://www.fda.gov/downloads/Drugs/Guidances/UCM070337.pdf>.
Partial European Search Report and Communication Communication pursuant to Rule 164(1) EPC iisued in related European Patent Application No. 17859772.0, dated Apr. 23, 2020.
Japanese Office Action issued in related Application No. JP 2019-520116, dated Nov. 17, 2020.
Oda, "Study of Organic Basic Reaction (9th Report)," Journal of the Chemical Society of Japan, 1954, vol. 75(10): pp. 987-989. (English translation included).
Barium, Element information, properties and uses, Periodic Table; Royal Society of Chemistry 2023, [online], [retrieved on Jan. 25, 2023]. Retrieved from the Internet: <URL: https://www.rsc.org/periodic-table/element/56/barium>.
Jaishankar et al. "Toxicity, mechanism and health effects of some heavy metals," Interdiscip Toxicol., 2014; 7(2): pp. 60-72.
12996 Chemical Products, Jan. 24, 1996, p. 423 (Document showing well-known art).
Barbagallo et al., "Magnesium and Aging," Current Pharmaceutical Design, 2010; 16(7): pp. 832-839. (abstract only).
Bardgett et al., "A temporal approach to linking aboveground and belowground ecology," TRENDS in Ecology and Evolution, 2005; 20(11): pp. 634-641.
Barrie et al., "Comparative absorption of zinc picolinate, zinc citrate and zinc gluconate in humans," Agents and Actions, 1987; 21(1/2): pp. 223-228.
Bergström et al., "Drug Targeting to the Brain: Transfer of Picolinic Acid Along the Olfactory Pathways,: Journal of Drug Targeting," 2002; 10(6): pp. 469-478.
Brilla et al., "Effects of a Novel Zinc-Magnesium Formulation on Hormones and Strength," Journal of Exercise Physiology Online, 2000; 3(4): pp. 26-36.
Deepmala et al., "Protective effect of combined therapy with dithiothreitol, zinc and selenium protects acute mercury induced oxidative injury in rats," Journal of Trace Elements in Medicine and Biology, 2013; 27: pp. 249-256.
Deloume et al., "Structure du picolate de magnésium dihydraté," Acta Cryst. B, 1973; 29: pp. 668-673. (English abstract included).
Farvid et al., "The impact of vitamin and/or mineral supplementation on lipid profiles in type 2 diabetes," Diabetes Res Clin Pract., 2004; 65(1): pp. 21-28.
Giovannucci et al., "Nutritional Predictors of Insulin-like Growth Factor I and Their Relationships to Cancer in Men," Cancer Epidemiol Biomarkers Prev., 2003; 12: pp. 84-89.
International Search Report and Written Opinion dated Jul. 15, 2020 in International Patent Application No. PCT/US20/31191.
Kadhim et al., "Effects of melatonin and zinc on lipid profile and renal function in type 2 diabetic patients poorly controlled with metformin," J. Pineal Res., 2006; 41: pp. 189-193.
Koehler et al., "What is Technological Pedagogical Content Knowledge?" Contemporary Issues in Technology and Teacher Education, 2009; 9(1): pp. 60-70.
Kong et al., "Thermochemistry on the Solid State Coordination Compounds M(Nic)2 ? H2O(s) (M=Mn and Mg, Nic= Nicotinate),"Journal of Physical Chemistry, 2009 , vol. 223, No. 6,pp. 675-688.
Sahin et al., "The Effect of Magnesium, Zinc, and Selenium, Used Alone or in Combination, on Strength and Anabolic Hormone Levels in Rats," The FASEB Journal, 2019; 33(51): pp. 839.7-839.7.
Schrauzer, "Selenomethionine: A Review of its Nutritional Significance, Metabolism and Toxicity," J Nutr., 2000; 130(7): pp. 1653-1656.
Swiderski et al., "Experimental (FT-IR, FT-Raman, 1H NMR) and theoretical study of magnesium, calcium, strontium, and barium picolinates," Spectrochimica Acta Part A: Molecular and Biomolecular Spectroscopy, 2006; 64: pp. 24-33.
Xu et al., "Magnesium Protects Cognitive Functions and Synaptic Plasticity in Streptozotocin-Induced Sporadic Alzheimer's Model," PLOS ONE, 2014; 9(9): pp. 1-11.

* cited by examiner

Figure 4
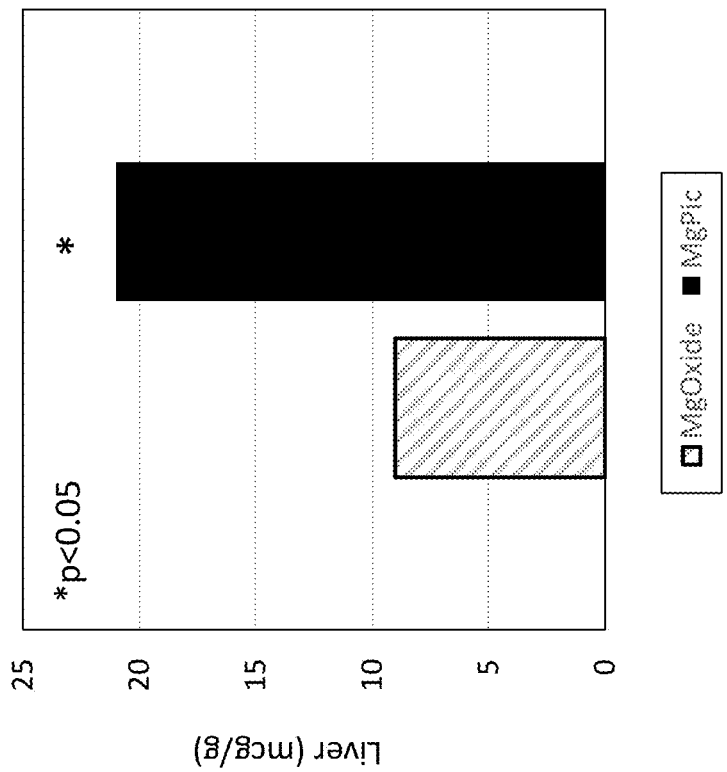
Figure 4B
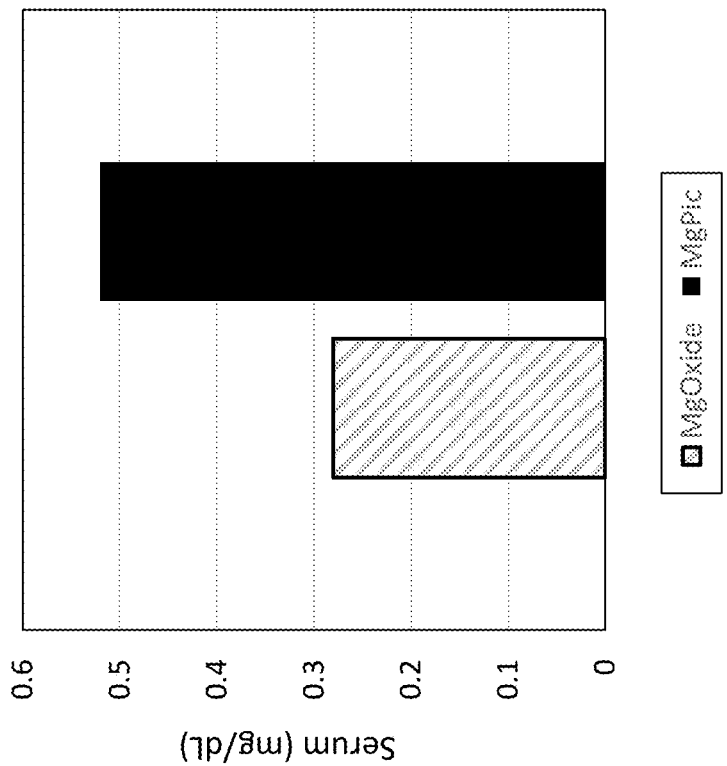
Figure 4A

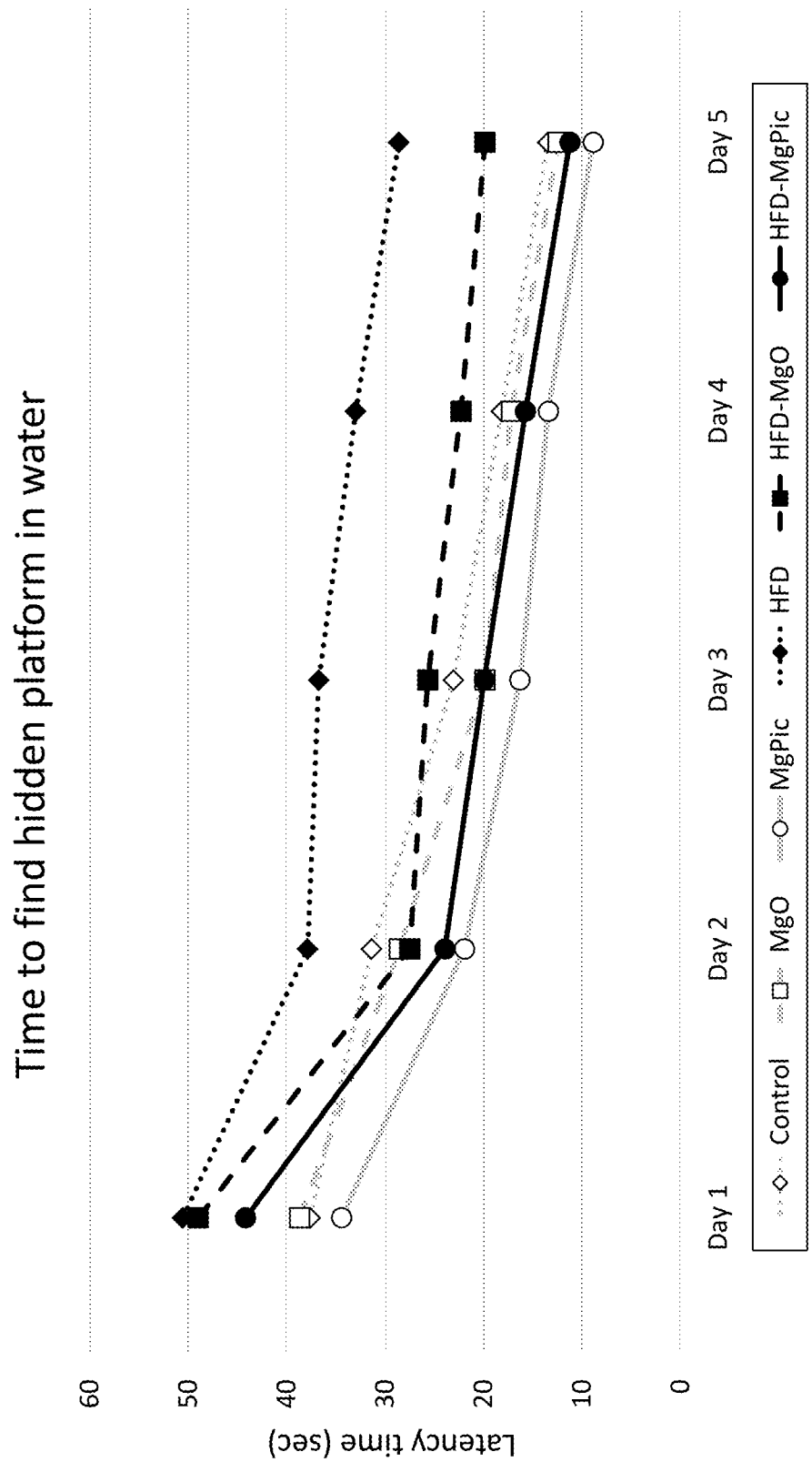

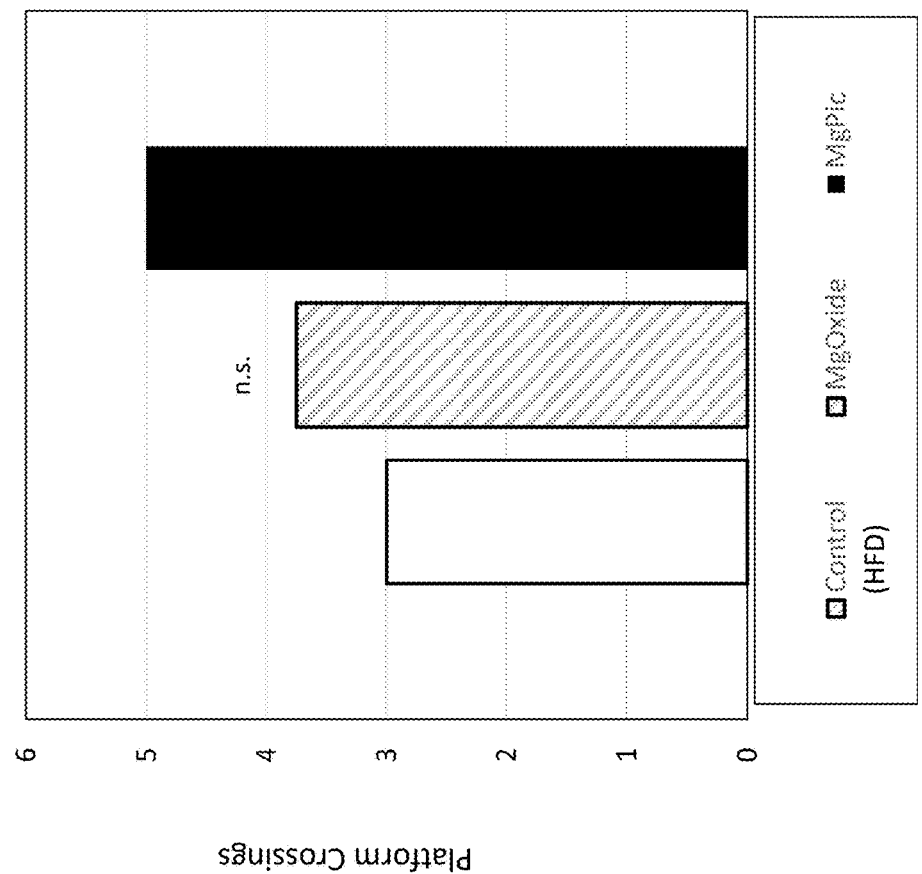

MAGNESIUM PICOLINATE COMPOSITIONS AND METHODS OF USE

CROSS-REFERENCE TO RELATED APPLICATIONS

This application claims priority to of U.S. Provisional Application No. 62/407,362 filed Oct. 12, 2016, the contents of which is incorporated by reference herein in its entirety.

BACKGROUND

Field

The present application relates to magnesium picolinate (MgPic) compositions and methods of use. The methods and compositions disclosed herein are particularly useful for providing bioavailable magnesium to mammals and treating or preventing symptoms of magnesium deficiency.

Description of the Related Art

Magnesium is an abundant mineral that occurs naturally both in the body and in many foods but compositions disclosed herein do not occur naturally and, as further described herein, prior methods of synthesis have failed to produce adequate compositions. Magnesium is an essential co-factor in many physiological processes, including energy production, protein synthesis and transport, cell signaling, and homeostatic regulation. Indeed, magnesium exhibits bioactivity in all cells and tissues of the body.

Dietary magnesium may be obtained from milk, oatmeal, fruits, vegetables, nuts, and seeds. Uptake of magnesium occurs primarily in the small intestine and secondarily in the large intestine. Most absorption is paracellular, although some is transcellular, through the TRPM channels. Magnesium absorption in the gastrointestinal tract is normally between 25-75%.

Despite its abundance in nature, magnesium deficiency is a widespread heath concern across the United States and globally. According to recent estimates, more than half of Americans are magnesium deficient. Magnesium deficiency is most common amongst individuals with elevated excretion of nutrients from the gastrointestinal tract (e.g., diarrhea). Thus, individuals having, for example, Crohn's disease, celiac disease, type II diabetes, and alcoholism frequently exhibit magnesium deficiency.

Magnesium deficiency and/or impaired magnesium utilization can have serious physiological consequence. For example, decreased magnesium levels in the brain have been associated with migraines, stroke, depression, Parkinson's, and other neurological disorders. Decreased magnesium levels in the lungs are associated with asthma and COPD. Decreased magnesium levels in the heart are associated with coronary artery disease, myocardial infarction, and abnormal blood flow. A decreased magnesium level in muscle is associated with cramps. A decreased magnesium level in bone is associated with osteoporosis.

Recommended values of magnesium intake (RDA) are approximately 400 mg for males and 310-320 mg for females, per day. Should dietary intake and absorption from the gastrointestinal tract fail to provide sufficient magnesium to meet physiological requirements, magnesium may be administered in supplements in a salt form, such as in magnesium oxide, magnesium citrate, magnesium glycinate, magnesium L-threonate, magnesium chloride, and the like. These salts differ from each other with respect to percent composition magnesium and bioavailability/absorption from the intestine.

In addition to differences in bioavailability from the gastrointestinal tract, magnesium compounds differ in their ability to cross the blood-brain barrier and increase magnesium levels in the brain. This is particularly important given the role of magnesium in maintaining proper neurological function. For example, the N-methyl-D-aspartate (NMDA) receptor is a glutamate receptor and ion channel protein found in nerve cells. This receptor is thought to be critical in synaptic plasticity, the cellular mechanism for learning and memory. The NMDA receptor is activated when glutamate and glycine (or D-serine) bind to it, and when activated it allows positively charged ions, such as $Na^{+2}$ and $Ca^{+2}$, to cross the cell membrane.

Magnesium plays a role in the open and closing of this ion channel. Specifically, the current flow through the activated (ligand-bound) ion channel is voltage dependent. Extracellular magnesium ($Mg^{+2}$) and zinc ($Zn^{+2}$) ions bind to sites on the receptor, blocking the passage of other (signaling) cations through the ion channel. Ultimately, depolarization of the cell repels the magnesium and zinc ions from the pore, allowing a voltage-dependent flow of signaling cations into the cell and potassium ($K^+$) out of the cell.

Moreover, calcium influx into these nerve cells causes translocation of α-amino-3-hydroxy-5-methyl-4-isoxazole-propionic acid receptors (AMPA) to the neuronal membrane. AMPA receptors also bind the excitatory neurotransmitter glutamate, causing a stronger response to glutamate and thus more excitation. However, decreased magnesium levels in the brain causes decreased blocking of NMDA receptors, permitting a constant influx of calcium, recruitment of AMPA receptors, and an increased response to glutamate. This overstimulation causes degeneration of proteins in the neuron and eventually neuronal death. Indeed, malfunction of the NMDA receptor has been linked to Alzheimer's disease, depression, migraine, and other diseases.

Research also suggests that picolinic acid is involved in the NMDA pathway, where it acts as a neuroprotective agent. Specifically, data suggest that picolinic acid is an antagonist of the NMDA receptor agonist quinolinic acid, a potent neurotoxin. As an antagonist to quinolinic acid, picolinic acid may block the effects of overstimulation of the NMDA receptor.

Two methods for the preparation of MgPic are known. In Deloume et al., magnesium carbonate was added to a hot, dilute solution of picolinic acid. The reaction mixture was slowly evaporated to dryness to provide MgPic. The solid was recrystallized twice to obtain colorless crystals for crystallographic study. See *Acta Crystallogr, Section B, Struct. Crystallogr Cryst. Chem.*, 29(4): 668-676 (1973). However, this method lacks sufficient detail to repeat in compliance with current Good Manufacturing Practices (cGMP).

Alternatively, according to Swiderski, et al., MgPic may be prepared by an exchange reaction between magnesium sulfate and barium picolinate in water. See *Spectrochim. Acta Part A*, 64(1): 24-33 (2006). However, this preparation of MgPic lacks certain features required to render it useful for pharmaceutical and/or nutraceutical applications today. For example, compounds adequate for human consumption must be free of metal contaminants such as barium. Thus, Swiderski's procedure would require extensive additional purification and testing to render the process useful for any pharmaceutical or nutraceutical application of MgPic.

Thus, there is a long-standing and unmet need for magnesium and picolinic acid compositions to provide enhanced bioavailability of magnesium, and enhanced bioavailability of picolinic acid, particularly to the brain.

SUMMARY

In some embodiments, the present invention comprises nutritional and therapeutic compositions that are useful for enhancing the bioavailability and/or brain penetration of magnesium and picolinic acid. Methods disclosed herein include enhancing the bioavailability of magnesium and picolinic acid by providing magnesium and picolinic acid as magnesium picolinate (MgPic) compositions. Methods for enhancing the bioavailability of magnesium and picolinic acid are also disclosed and may comprise administering to a subject a safe and effective amount of a MgPic composition. Further, a method of enhancing the bioavailability of magnesium and picolinic acid in warm-blooded animals is disclosed. Such a method may comprise administering a therapeutically effective amount of a pharmaceutical composition comprising a MgPic composition. In addition, the present invention may provide a nutritional and therapeutic MgPic composition that is useful for enhancing the bioavailability of magnesium and picolinic acid. The composition may be useful, for example, in mammals.

In some aspects, the compositions disclosed herein may be used to treat or prevent magnesium deficiencies. For example, the compositions may be administered to restore depleted magnesium levels caused by the administration of one or more other drugs. The compositions may also be used to use treat or prevent, diseases such as Alzheimer's disease and other diseases associated with defects in NMDA receptor signaling and/or associated with nerve damage. Other features, advantages, and embodiments of the invention will be apparent to those of ordinary skill in the art from the following description, examples, and appended claims.

Some embodiments provide a composition comprising pharmaceutical quality magnesium picolinate and a pharmaceutically acceptable vehicle, carrier, or diluent. In some embodiments, the composition is a solid composition.

In some embodiments, the composition comprises a sustained-release matrix. In some embodiments, the composition is enteric coated. In some embodiments, the composition comprises between about 10 μg to about 1,000 μg of magnesium picolinate.

In some embodiments, the composition comprises no more than 200 parts per million (ppm) of any heavy metal selected from the group consisting of cadmium, mercury, lead, nickel, arsenic, cobalt, antimony, thallium, barium, silver, selenium, copper, zinc, manganese, strontium, or combination of the foregoing.

Some embodiments provide a method of treating or preventing a disease, disorder, or condition associated with magnesium deficiency in a mammal known to have or be at risk for developing magnesium deficiency, comprising administering an amount of pharmaceutical quality magnesium picolinate effective to treat or prevent a disease, disorder, or condition associated with magnesium deficiency in the mammal. Some embodiments comprise administering a composition as described herein for improving memory function. Some embodiments comprise administering a composition described herein for restoring impaired memory function. Impaired memory function can be a result of Alzheimer's disease, aging, poor diet, or other cognitive disorders. Certain embodiments comprise administering a composition as described herein to improve metabolic function.

In some embodiments, the disease, disorder, or condition, is a cognitive condition. In some embodiments, the cognitive condition is selected from the group consisting of Alzheimer's disease, migraines, stroke, depression, Parkinson's disease, schizophrenia, traumatic brain injury, post-traumatic stress disorder, Huntington's disease, or combinations of the foregoing.

In some embodiments, the disease, disorder, or condition, is selected from the group consisting of fibromyalgia, post-amputation phantom pain, pain due to nerve damage, hyperexcitability, fatigue, loss of appetite, cramps, muscle tremors, muscle spasms, tetany, muscle weakness, fasciculations, insomnia, confusion, irritability, hypertension, osteoporosis, diabetes, coronary heart disease, chronic inflammation, preeclampsia, myocardial infarction, asthma, renal disease, Bartter's syndrome, Gitelman syndrome, long-term administration of loop diuretics, long-term administration of thiazide diuretics, administration of cisplatin, administration of aminoglycosides, administration of cyclosporin, alcoholism, long-term administration of proton pump inhibitors, or combinations of the foregoing. Some embodiments comprise administering a composition as described herein for reducing body fat. Some embodiments comprise administering a composition as described herein for reducing leptin secretion. Some embodiments comprise administering a composition as described herein for increasing a subject's magnesium levels. Some embodiments comprise administering a composition as described herein for increasing a subject's liver magnesium levels. Some embodiments comprise administering a composition as described herein for increasing a subject's brain magnesium levels. Some embodiments comprise administering a composition as described herein for increasing a subject's brain antioxidant enzyme catalase (CAT) levels. Some embodiments comprise administering a composition as described herein for increasing a subject's brain antioxidant enzyme GSH-Px levels. Some embodiments comprise administering a composition as described herein for reducing body fat. Some embodiments comprise administering a composition as described herein for reducing visceral fat. Some embodiments comprise administering a composition as described herein for reducing blood glucose levels. Some embodiments comprise administering a composition as described herein for reducing blood insulin levels.

In some embodiments, the amount of magnesium picolinate administered is between about 10 μg to about 1,000 μg per day. In some embodiments, the magnesium picolinate is administered orally.

Some embodiments provide a method of making pharmaceutical quality magnesium picolinate comprising: combining picolinic acid and magnesium acetate tetrahydrate in a solution, and optionally removing water. Some embodiments provide a method of making nutraceutical quality magnesium picolinate comprising: combining picolinic acid and magnesium acetate tetrahydrate in a solution, and optionally removing water.

In some embodiments, the picolinic acid consists of an aqueous solution of picolinic acid. In some embodiments, the magnesium acetate tetrahydrate consists of an aqueous solution of magnesium acetate tetrahydrate. Some embodiments further comprise removing water. In some embodiments, removing water comprises heating the mixture, placing the mixture under vacuum, or a combination thereof. In some embodiments, the pharmaceutical quality magnesium picolinate is crystalline. In some embodiments, the pharmaceutical quality magnesium picolinate is amorphous.

Some embodiments provide a method of making pharmaceutical and/or nutraceutical quality magnesium picolinate comprising: combining picolinic acid and magnesium ethoxide in a solution, and optionally removing one or more solvents, and wherein the method does not include further steps to remove other heavy metals.

Some embodiments provide a method of making pharmaceutical and/or nutraceutical quality magnesium picolinate comprising: dissolving picolinic acid in water to form a picolinic acid solution; adding a basic solution to the picolinic acid solution such as, but not limited to, NaOH; dissolving magnesium chloride hexahydrate in water to form a magnesium chloride hexahydrate solution; filtering the magnesium chloride hexahydrate solution and then adding the filtrate to the picolinic acid solution to form a solution; heating the solution; cooling the picolinic acid solution; filtering the solution; and drying the residue. The method of preparing the magnesium picolinate may produce a composition comprising less than about 200 ppm of barium and/or other heavy metals. In some embodiments, these compositions may comprise less than about 150, less than about 100, less than 50, or less than 20 ppm of barium and/or other heavy metals.

Some embodiments provide a method of making pharmaceutical and/or nutraceutical quality magnesium picolinate comprising: combining picolinic acid and magnesium oxide in water to produce a slurry; heating the slurry; adding water to the slurry; cooling the slurry; filtering the slurry; and drying the residue under vacuum. The cooling step can be overnight. The method can further comprise dissolving the residue in ethanol to produce an ethanol solution; filtering the ethanol solution; and precipitating the magnesium picolinate with water. The method of preparing the magnesium picolinate may produce a composition comprising less than about 200 ppm of barium and/or other heavy metals. In some embodiments, these compositions may comprise less than about 150, less than about 100, less than 50, or less than 20 ppm of barium and/or other heavy metals.

In some embodiments, the picolinic acid consists of an ethanolic solution of picolinic acid. In some embodiments, the magnesium ethoxide is a solid. In some embodiments, the magnesium ethoxide comprises an ethanolic solution of magnesium ethoxide. In some embodiments, the method comprises removing one or more solvents. In some embodiments, the one or more solvents are independently selected from water, ethanol, methanol, isopropanol, and t-butanol.

In some embodiments, removing one or more solvents comprises heating the mixture, placing the mixture under vacuum, or a combination thereof. In some embodiments, the pharmaceutical quality magnesium picolinate is crystalline. In some embodiments, the pharmaceutical quality magnesium picolinate is amorphous.

BRIEF DESCRIPTION OF THE DRAWINGS

FIG. 5 shows the time taken by rats to find a hidden platform in a water tank and shows the improvements achieved using magnesium picolinate.

FIG. 6 shows the memory improvements achieved by rats after receiving magnesium picolinate where the rats had impaired memory function resulting from a high fat diet.

DETAILED DESCRIPTION

Figure 1:
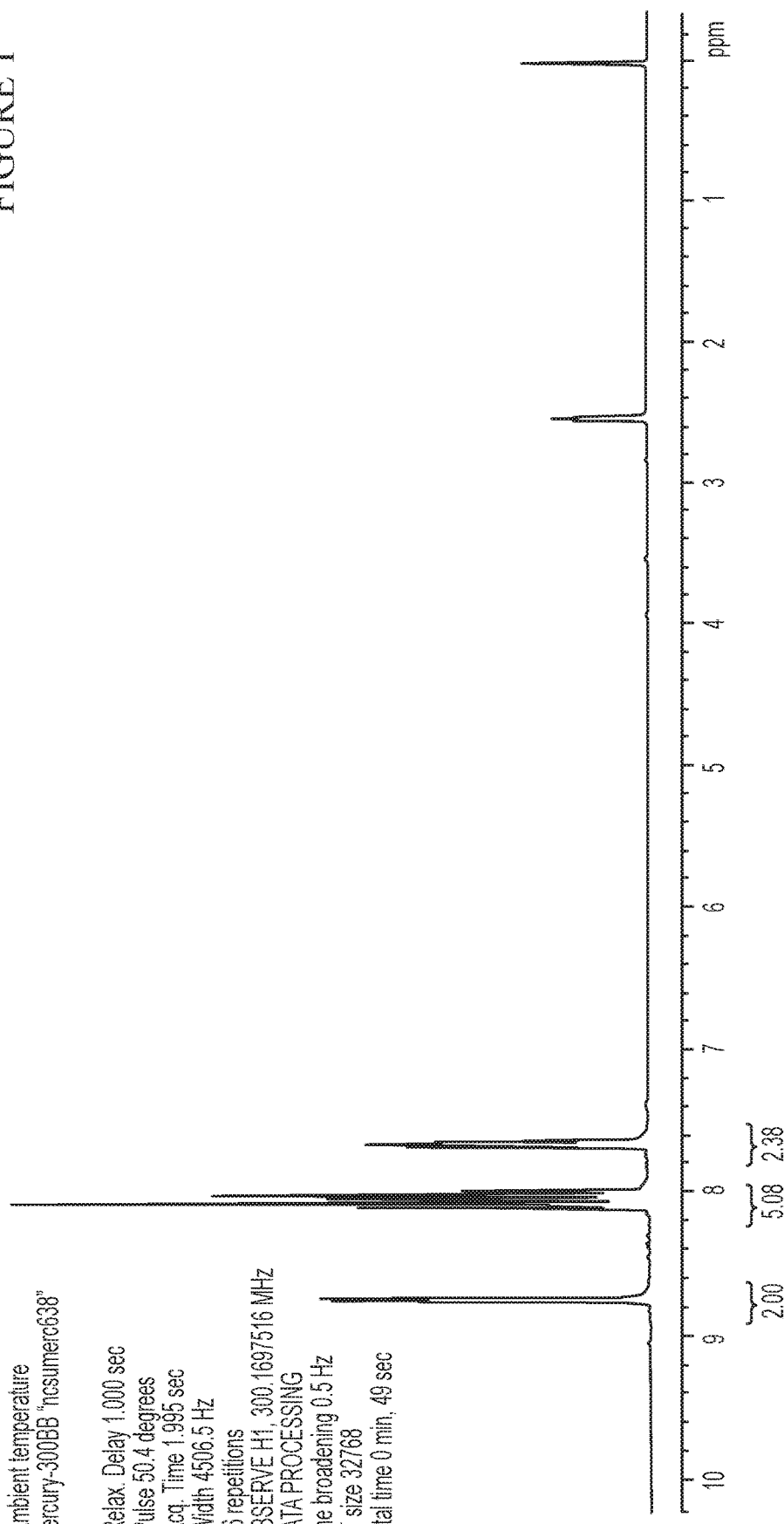
FIG. 1 depicts a $^1$H-NMR spectrum of picolinic acid.

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the embodiments described herein.

As used herein, "identifying," refers to detecting or selecting a subject from a population of potential subjects, for example, to establish that a particular subject possesses certain properties or characteristics. "Identifying" may include, for example, self-identification, self-diagnosis, and diagnosis by a medical professional.

As used herein, "treat," "treatment," or "treating," refers to administering or providing a composition for prophylactic and/or therapeutic purposes. The term "treatment" as used herein can encompass any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms, conditions, and co-morbidities As used herein, the terms "prophylactic treatment," "prevent," or "preventing," can refer to treating a subject who does not yet exhibit symptoms of a disease or condition, but who is susceptible to, or otherwise at risk of, a particular disease or condition, whereby the treatment reduces the likelihood that the patient will develop the disease or condition. A "disorder" is any condition that would benefit from treatment with the compositions described herein.

As used in the claims below and throughout this disclosure, the phrase "consisting essentially of" is meant to include any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and can or cannot be present depending upon whether or not they affect the activity or action of the listed elements. For example, the use of a composition "consisting essentially of magnesium picolinate" for the treatment of a particular disease or disorder would exclude other ingredients that were known to be active in combating the particular disease or disorder.

As used herein, a composition that "substantially" comprises a compound means that the composition contains more than about 80% by weight, more preferably more than about 90% by weight, even more preferably more than about 95% by weight, and most preferably more than about 98% by weight of the compound.

The term "about," unless otherwise stated explicitly herein, means±20%. For instance about 100 means 80 to 120, about 5 means 4 to 6, about 0.3 means 0.24 to 0.36, and about 60% means 48% to 72% (not 40% to 80%).

The term "pharmaceutical formulation" refers to preparations which are in such a form as to permit the biological activity of the active ingredients to be effective, and, therefore may be administered to a subject for therapeutic use.

A "therapeutically effective amount" as used herein includes within its meaning a non-toxic but sufficient amount of a compound active ingredient or composition comprising the same for use in the embodiments disclosed herein to provide the desired therapeutic effect. Similarly "an amount effective to" as used herein includes within its meaning a non-toxic but sufficient amount of a compound active ingredient or composition comprising the same to provide the desired effect. The exact amount of the active ingredient disclosed herein required will vary from subject to subject depending on factors such as the species being treated, the age and general condition of the subject, the severity of the condition being treated, the particular agent being administered, the weight of the subject, and the mode of administration and so forth. Thus, it is not possible to specify an exact "effective amount." However, for any given case, an appropriate "effective amount" may be determined by one of ordinary skill in the art using only routine methods. In some aspects, a therapeutically effective amount may include a dosing regimen. "Therapeutically effective" can be intended to qualify the amounts of a MgPic composition which will achieve the goal of providing the quantity of magnesium and picolinic acid, or a salt thereof, needed to prevent and treat adverse effects associated with magnesium deficiency. The amounts of a MgPic composition may be administered orally to a subject as part of the same unit dose or as different unit doses administered in a coordinated manner. Further, the amounts of a MgPic composition may be administered in a coordinated manner by different routes of administration, if required to ensure bioavailability in a subject requiring this treatment. By way of example, administration in a coordinated manner may comprise oral administration of an effective amount of a MgPic composition at a time point and administration of an effective amount of a MgPic composition by oral, transdermal, or intravenous administration at a separate time point within 72 hours of administration of the first effective amount of said composition For example, a therapeutically effective amount may include about 1 mg of MgPic orally consumed each day for fourteen consecutive days. In some aspects, a therapeutically effective amount may include about 1 mg of MgPic orally consumed each day for thirty consecutive days. Compositions including MgPic may include, for example, between 0.1-10 grams of MgPic. It should also be noted that the dosage of MgPic can be configured for a desired amount of elemental magnesium. For example, one gram of MgPic would contain 9% elemental Mg by weight (i.g., 0.09 g of Mg in the 1 g of MgPic). Given this relationship, one of ordinary skill in art would understand the dosage amounts and weights given in the disclosure to include the amount of magnesium alone or the mass of a MgPic composition, and would readily ascertain these values in view of the context in which these terms are used.

In addition, the appropriate dosage of the compositions will depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition is suitably administered to the patient at one time or over a series of treatments and may be administered to the patient at any time from diagnosis onwards. The composition may be administered as the sole treatment or in conjunction with other drugs or therapies useful in treating the condition in question.

By way of example, a "therapeutically effective amount" of the compound disclosed herein can be, for example, 0.1 µg/kg, 0.5 µg/kg, 1 µg/kg, 1.5 µg/kg, 2.0 µg/kg, 2.5 µg/kg, 3.0 µg/kg, 3.5 µg/kg, 4.0 µg/kg, 4.5 µg/kg, 5.0 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 80 µg/kg 0, 850 µg/kg, 900 µg/kg, 1 mg/kg, 1.5 mg·kg, 2.0 mg/kg, 2.5 mg/kg, 3 mg/kg, 3.5 mg/kg, 4.0 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, or more, or any fraction in between of the compound (e.g., wherein the compound can refer to a MgPic compound).

Accordingly, in some embodiments, the dose of the compound in compositions disclosed herein can be about 10 µg to about 10 g, preferably per day. For example, the amount of the complex can be 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, 15 g, 20, g, 30 g, 40 g, 50 g or more, or any range or amount in between any two of the preceding values. For example, a dose may comprise between about 10 µg and 100 µg, about 1,000 µg to about 10,000 µg, about 10 mg and 100 mg, about 100 mg and about 1000 mg, about 50 mg to about 1000 mg, about 500 and about 1000 mg, about 1 g to about 50 g, and ranges therebetween. The exemplary therapeutically effective amounts listed above, can, in some embodiments be administered in the methods described elsewhere herein on an hourly bs, e.g., every one, two, three, four, five, six, seven, eight, nine, ten, eleven, twelve, thirteen, fourteen, fifteen, sixteen, seventeen, eighteen, nineteen, twenty, twenty-one, twenty-two, twenty-three hours, or any interval in between, or on a daily basis, every two days, every three days, every four days, every five days, every six days, every week, every eight days, every nine days, every ten days, every two weeks, every month, or more or less frequently, as needed to achieve the desired therapeutic effect.

The present invention provides methods for the preparation and use of pharmaceutical quality MgPic compositions that contain at most trace levels of metal contaminants selected from the group consisting of aluminum, arsenic, barium, cadmium, chromium, lead, mercury, and thallium. Therefore, a composition of the invention overcomes the drawbacks of prior art compositions in which unacceptably high levels of barium and other toxic metals are present.

Methods of preparation of pharmaceutical quality MgPic compositions comply with current Good Manufacturing Practices (cGMP).

The present invention comprises nutritional and therapeutic compositions useful for enhancing the bioavailability of magnesium and picolinate. Methods are disclosed for enhancing the water-solubility of magnesium and picolinate by providing both magnesium and picolinate as MgPic compositions. Methods for enhancing the bioavailability of magnesium and picolinate are also disclosed, comprising administering to a subject a safe and effective amount of a MgPic composition. Further, a method of enhancing the bioavailability of magnesium and picolinate in a warm-blooded animal is disclosed, comprising administering a therapeutically effective amount of a pharmaceutical quality composition comprising a pharmaceutical quality MgPic composition. In addition, the present invention provides a nutritional and therapeutic, water-soluble MgPic composition useful for enhancing the bioavailability of both magnesium and picolinate in the brain. The composition is useful in mammals.

As used herein, the term "magnesium picolinate," or "MgPic," refers to a magnesium salt having the molecular formula $Mg(C_6H_4NO_2)_2$, a mass of 268.508 g/mol, and the general formula:

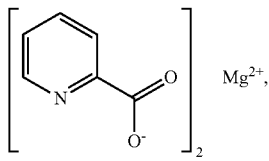

along with physiologically compatible hydrates, crystalline forms, polymorphic forms, solid forms having specific bulk densities or tap densities, and solid forms having specific particle sizes.

Other common names for MgPic are 2-pyridinecarboxylic acid, magnesium salt; di(2-pyridinecarboxylate) de magnesium; magnesium di(2-pyridinecarboxylate); magnesium dipyridine-2-carboxylate; and magnesium bis(pyridine-2-carboxylate).

As used herein, the term "picolinate" refers to the conjugate base of picolinic acid. Picolinic acid has Chemical Abstracts Service Registry No. 98-96-6, the molecular formula $C_6H_5NO_2$, and the general formula:

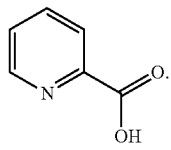

As used herein, the term "pharmaceutical quality" refers to a material that is safe to administer to humans without further processing. For example, pharmaceutical quality magnesium picolinate is safe to administer without further processing such as removing any metals or other contaminants. Pharmaceutical quality may also, in some implementations, refer to a substance that is manufactured in compliance with current Good Manufacturing Practices (cGMP). See *Guidance for Industry—Quality Systems Approach to Pharmaceutical CGMP Regulations*, September 2008. In addition, in some implementations, the term refers to a substance that is manufactured in compliance with current regulations relating to elemental impurities. See *Guidance for Industry—Q3D Elemental Impurities*, September 2015.

As used herein, the term "trace level" refers to the concentration of an element that is present in a substance. Acceptable trace levels will differ by element. In general, the term refers to a concentration of a metallic element other than magnesium that is less than about 200 micrograms per gram of a substance.

As used herein, the term "heavy metal" refers to metals including, but not limited to, cadmium, mercury, lead, nickel, arsenic, cobalt, antimony, thallium, chromium, barium, silver, selenium, copper, zinc, manganese, strontium, and salts or combinations thereof.

As used herein, the term "cognitive condition" refers to a disease, disorder, or condition primarily affecting learning, memory, perception, and/or problem solving, which may include amnesia, dementia, and/or delirium.

Some embodiments provide physiologically compatible MgPic hydrates, crystalline forms, polymorphic forms, solid forms having specific bulk densities or tap densities, and solid forms having specific particle sizes. Some embodiments provide compositions coated with pharmaceutically acceptable materials intended to modify its release and/or bioavailability, including, but not limited to Eudragit, microcrystalline cellulose, hydroxypropylmethylcellulose phthalate, and the like.

As used herein, the term "magnesium" refers to the magnesium ion, $Mg^{2+}$.

As used herein, the term "pharmaceutically acceptable solvent" is meant water, water for injection, aqueous buffer solutions that are physiologically compatible, as well as aqueous solutions containing organic solvents that are physiologically compatible. A non-comprehensive list of pharmaceutically acceptable solvents is provided in U.S. Department of Health & Human Services, Food & Drug Administration, "Guidance for Industry: Q3C Impurities: Residual Solvents," December 1997.

As used herein, the term "bioavailability" refers to the amount of a substance that is absorbed in the intestines and ultimately available for biological activity in a subject's tissue and cells.

As used herein, the term "enhancing the bioavailability" and the like are used herein to refer to obtaining a desired pharmacological and physiological effect of increasing the amount of magnesium that is absorbed from the intestine or is taken up by tissues and cells after administration of a composition to a mammal. The effect may be prophylactic in terms of preventing or partially preventing the incidence, risk, or severity of an adverse symptom or condition caused by or related to the deficiency of a therapeutic agent.

As used herein, the term "enhancing brain penetration" and the like are used herein to refer to a particular sub-type of bioavailability. Specifically, to obtaining a desired pharmacological and physiological effect of increasing the amount of magnesium that crosses the blood-brain barrier after administration of a composition to a mammal. The effect may be prophylactic in terms of preventing or partially preventing the incidence, risk, or severity of an adverse symptom or condition caused by or related to the deficiency of a therapeutic agent.

As used herein, the term "excipient material" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

For the purpose of this disclosure, a warm-blooded animal is a member of the animal kingdom which includes but is not limited to mammals and birds. The most preferred mammal of this application is a human.

As used herein, the term "nutraceutical" and "pharmaceutical" can be used interchangeably and distinctly, and their meaning will be clear to the skilled artisan in consideration of the context in which they are used. For example, a "pharmaceutically acceptable solvent" can be interpreted to include a "nutraceutically acceptable solvent" but not necessarily vice versa. The compositions described herein may be referred to as "nutraceuticals" or "dietary supplements" and these terms may be used interchangeably. "Pharmaceutical" can encompass "nutraceutical" and "nutraceutical" can encompass a "dietary supplement" but neither a "dietary supplement" nor a "nutraceutical" can be a "pharmaceutical." When describing nutraceuticals and dietary supplements, these terms are to be interpreted in the manner that would be given to them by the skilled artisan and in consideration of the guidelines of the U.S. Food and Drug Administration. Nutraceutical and dietary supplement compositions described herein may also include ingredients or components that are defined as generally recognized as safe (GRAS).

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

A synthetic approach was developed in an attempt to minimize the volume of a pharmaceutically acceptable solvent that was required to prepare high-purity MgPic compositions. Such a pharmaceutically acceptable solvent for MgPic would preferably be compatible with solutions of magnesium salts to enable use of pharmaceutically acceptable solvents throughout the preparation.

Unexpectedly, the MgPic composition was not hygroscopic and was stable on exposure to light. Compositions were also stable during storage at 25° C./40% relative humidity as well as at 40° C./75% relative humidity.

The present invention is based, at least in part, on the surprising finding that the MgPic compositions described herein provide unexpectedly greater quantities of magnesium and picolinic acid after administration such as is described in the experiments contained herein. Thus, in some aspects, the MgPic composition increases the bioavailability of magnesium and of picolinic acid when compared to other known compositions. While not wishing to be bound to any particular hypothesis or theory, it is believed that the composition disclosed herein provides unexpectedly greater quantities of magnesium and of picolinic acid because of its water solubility at physiological pH. In some aspects, the presently disclosed compositions thus provide more bioavailable magnesium and picolinic acid than previous compositions.

Compositions capable of delivering more bioavailable magnesium may result in compositions having less amounts of total magnesium than previous composition and formulations. In this way, manufacturing costs may be decreased and subjects may be administered compositions comprising lower amounts of magnesium to achieve similar efficacy to compositions with more magnesium.

Compositions capable of delivering more bioavailable picolinic acid, or salts thereof, may result in compositions having less amounts of total picolinic acid than previous composition and formulations. In this way, manufacturing costs may be decreased and subjects may be administered compositions comprising lower amounts of picolinic acid to achieve similar efficacy to compositions with more picolinic acid.

Compositions capable of delivering more bioavailable magnesium and more bioavailable picolinic acid, or salts thereof, may result in compositions having less amounts of total picolinic acid, and less amounts of total magnesium, than previous composition and formulations. In this way, manufacturing costs may be decreased and subjects may be administered compositions comprising lower amounts of picolinic acid and magnesium to achieve similar efficacy to compositions with more picolinic acid and more magnesium.

The administration of one or more of the compositions disclosed herein can be by any of the methods of administration described herein or by delivery methods known by one of skill in the art. The compositions may be administered orally, through parenteral nutrition, e.g., feeding tube, intravenously, or topically, and through other known means.

For oral administration, the compositions disclosed herein can be provided as a tablet, aqueous or oil suspension, dispersible powder or granule, emulsion, hard or soft capsule, syrup, elixir, or beverage. Solid dosage forms such as tablets and capsules may comprise an enteric coating. Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents will increase the palatability of the preparation. Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin or non-gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the complex of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions can be formulated by suspending the active ingredient in a vegetable oil, such as *arachis* oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

The composition for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils can be employed conventionally as a solvent or suspending medium. For this purpose, any bland fixed oil can be employed including synthetic mono or diglycerides. In addition, fatty acids such as oleic acid can likewise be used in the preparation of injectable preparations.

It will be appreciated that the amount of the compound may be combined with a carrier material to produce a single dosage form. Such forms will vary depending upon the host treated and the particular mode of administration.

When administered to a mammal, e.g., to an animal for veterinary use or for improvement of livestock, or to a human for therapeutic use, the compositions disclosed herein can be administered in isolated form or as the isolated form in a therapeutic composition. As used herein, "isolated" means that the compositions disclosed herein are separated from other components of either (a) a natural source, such as a plant or cell or food, preferably bacterial culture, or (b) a synthetic organic chemical reaction mixture. Preferably, via conventional techniques, the compositions disclosed herein are purified. As used herein, "purified" means that when isolated, the isolate contains at least 95%, preferably at least 98% of the composition.

In some aspects, MgPic may be added to food that is designed for animals. For example, the compound or composition may be added to and/or comprise a pet treat or biscuit, for example, a dog biscuit or a cat treat Aqueous suspensions may contain the compound disclosed herein in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Controlled release vehicles are well known to those of skill in the pharmaceutical sciences. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, are also well known and can be used in the disclosed methods.

Controlled release preparations can be achieved by the use of polymers to form complexes with or absorb the MgPic. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active complex.

Controlled release of active complexes can be taken to mean any of the extended release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein MgPic is dissolved in an aqueous constituent to gradually release over time, can be prepared by copolymerization of hydrophilic mono-olefinic monomers such as ethylene glycol methacrylate. Matrix devices, wherein MgPic is dispersed in a matrix of carrier material, can be used. The carrier can be porous, non-porous, solid, semi-solid, permeable or impermeable. Alternatively, a device comprising a central reservoir of magnesium picolinate surrounded by a rate controlling membrane can be used to control the release of the complex. Rate controlling membranes include ethylene-vinyl acetate copolymer or butylene terephthalate/polytetramethylene ether terephthalate. Use of silicon rubber depots is also contemplated.

Controlled release oral formulations are also well known. In one embodiment, the active complex is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

Magnesium picolinate may also be delivery topically, including in a salve, cream, lotion, ointment, shampoo, solution, or emulsion.

The amount of a complex that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges.

The compositions may be administered once, twice, or three times per day. In some aspects, the compositions are administered four times a day. For example, the compositions may be administered before, after, or during a meal. Dosing for oral administration may be with a regimen calling for single daily dose, or for a single dose every other day, or for a single dose within 72 hours of the first administered dose, or for multiple, spaced doses throughout the day. The active agents which make up the therapy may be administered simultaneously, either in a combined dosage form or in separate dosage forms intended for substantially simultaneous oral administration. The active agents which make up the therapy may also be administered sequentially, with either active component being administered by a regimen calling for two-step ingestion. Thus, a regimen may call for sequential administration of the active agents with spaced-apart ingestion of the separate, active agents. The time period between the multiple ingestion steps may range from a few minutes to as long as about 72 hours, depending upon the properties of each active agent such as potency, solubility, bioavailability, plasma half-life and kinetic profile of the agent, as well as depending upon the age and condition of the patient. The active agents of the therapy whether administered simultaneously, substantially simultaneously, or sequentially, may involve a regimen calling for administration of one active agent by oral route and the other active agent by intravenous route. Whether the active agents of the therapy are administered by oral or intravenous route, separately or together, each such active agent will be contained in a suitable pharmaceutical formulation of pharmaceutically-acceptable excipients, diluents or other formulations components.

The active ingredients (i.e., MgPic and other pharmaceutical or supplemental ingredients that may be present) can be administered by the oral route in solid dosage forms, such as tablets, capsules, and powders, or in liquid dosage forms, such as elixirs, syrups, and suspensions. Each active ingredient can be administered by the parenteral route in liquid dosage forms. The pharmaceutical composition is preferably made in the form of a dosage unit containing a particular amount of each active ingredient. One most preferred oral dosage form of a composition of the present application is an admixture of powders contained within a sachet. Because a composition of the present application is not hygroscopic and has no repugnant taste or odor, the admixture of powders comprising a composition of the present application can be sprinkled on food or stirred into beverages to enhance ease of use and support high levels of compliance with daily dosage regimens.

In general, the pharmaceutical dosage forms of compositions of this application can be prepared by conventional techniques, as are described in *Remington's Pharmaceutical Sciences*, a standard reference in this field Gennaro A R, Ed. *Remington: The Science and Practice of Pharmacy*. 20$^{th}$ Edition. Baltimore: Lippincott, Williams & Williams (2000). For therapeutic purposes, the active components of this combination therapy application are ordinarily combined with one or more adjuvants appropriate to the indicated route of administration. The components may be admixed with lactose, sucrose, starch powder, cellulose esters of alkanoic acids, cellulose alkyl esters, talc, stearic acid, magnesium stearate, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl methylcellulose. Solid dosage forms can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance. Other adjuvants and modes of administration are well and widely known in the pharmaceutical art.

While the present invention has been described in some detail for purposes of clarity and understanding, one will appreciate that various changes in form and detail can be made without departing from the true scope of the invention.

EXAMPLES

Example 1. Attempted Preparation of Magnesium Picolinate According to Swiderski

According to Swiderski, MgPic may be prepared by an exchange reaction between magnesium sulfate and barium picolinate. Accordingly, a solution of barium picolinate was prepared by dissolving 2 mol equivalents of picolinic acid and 1 mol equivalent of barium hydroxide in 100 mL of water. When a clear solution of barium picolinate was obtained, 1 mol equivalent of magnesium sulfate powder was added. After stirring for 12 hours, the slurry was filtered to remove solid barium sulfate, the filtrate was concentrated to dryness, and the resulting solid was dried at 120° C. for 24 hours to provide anhydrous MgPic was obtained. The barium level in the anhydrous MgPic was found to be greater than 200 ppm. This far exceeds the pharmaceutical tolerance for barium contamination of about 200 ppm. Repeated dissolution and crystallization, which was attempted to reduce the level of barium contamination, resulted in the loss of almost 50% of the MgPic and failed to reduce the barium contamination to acceptable trace levels.

Example 2. Preparation A of Crystalline and Amorphous Magnesium Picolinate

Figure 2:
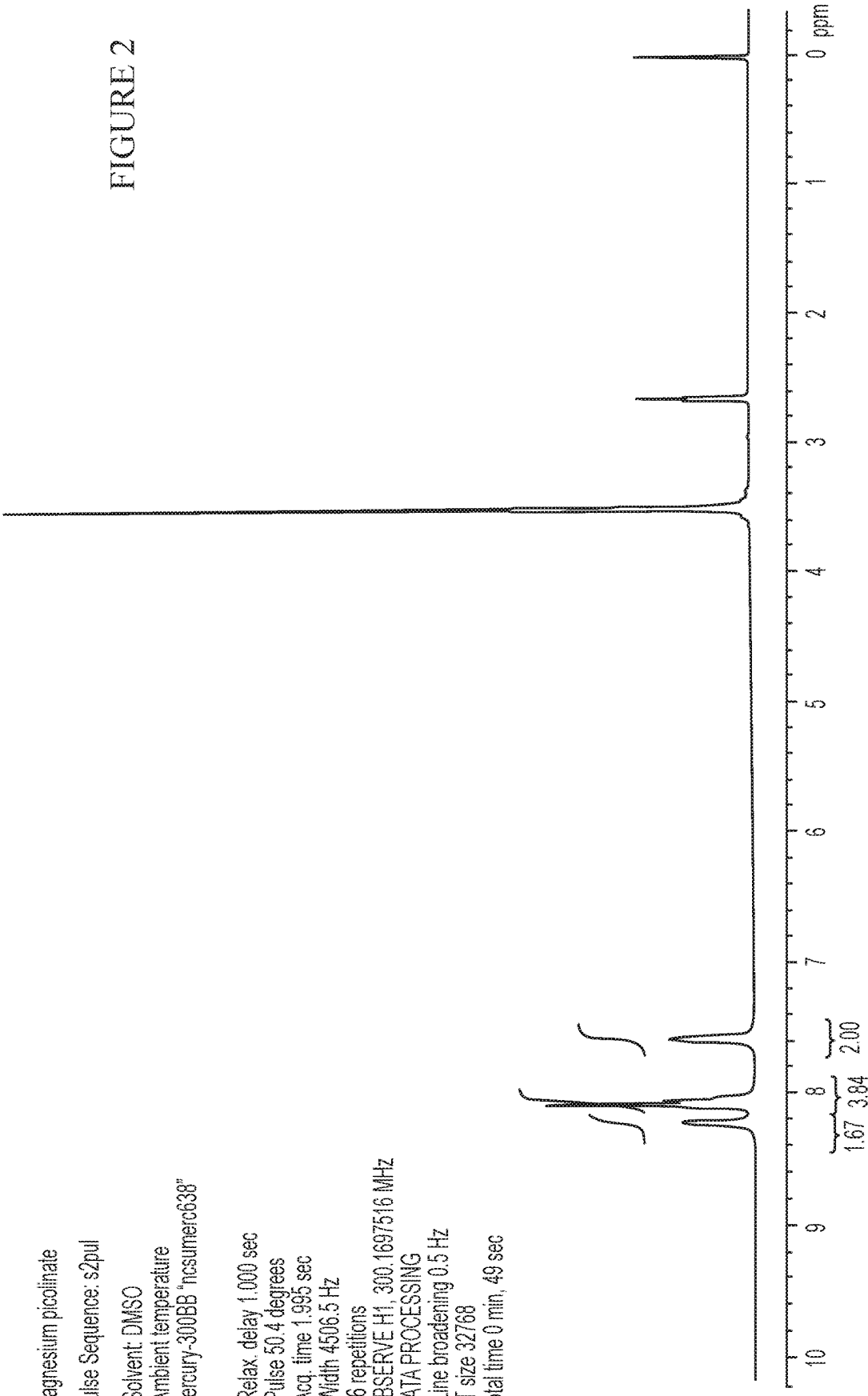
FIG. 2 depicts a $^1$H-NMR spectrum of a MgPic composition as disclosed in Example 2.

Picolinic acid (3.7 g, 30 mmol) and magnesium acetate tetrahydrate (3.2 g, 15 mmol) were suspended in 25 mL of water. The slurry was stirred and heated at reflux overnight and then filtered to isolate 1.7 grams of crystalline MgPic. The remaining filtrate was cooled and evaporated to dryness, providing an additional 2.2 grams of amorphous MgPic with traces of residual acetate. The acetate was removed by washing the solid with ethanol to provide a 96% overall yield of MgPic (crystalline and amorphous). The $^1$H-NMR spectrum of the product (FIG. 2) is consistent with the spectrum of a metal picolinate salt. The product was readily soluble in water and provided a clear and colorless solution of MgPic. The product contained acceptable trace levels of barium and other heavy metals of less than 200 ppm of each element tested. As such, embodiments of a MgPic composition may comprise less than about 200 ppm of barium and/or other heavy metals. In some embodiments, these compositions may comprise less than about 150, less than about 100, less than 50, or less than 20 ppm of barium and/or other heavy metals.

Example 3. Preparation B of Crystalline Magnesium Picolinate

Figure 3:
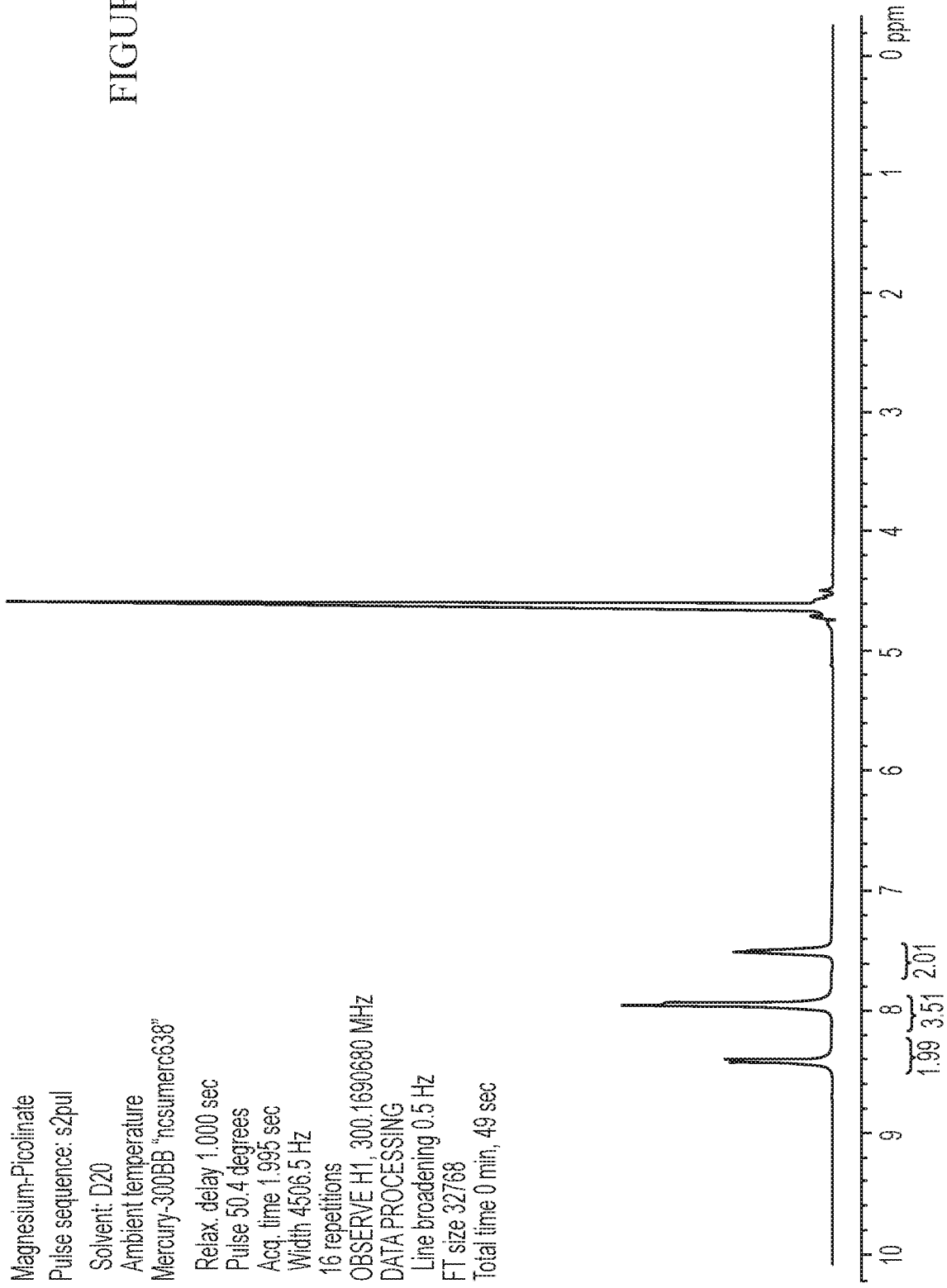
FIG. 3 depicts a $^1$H-NMR spectrum of a MgPic composition as disclosed in Example 3.

Picolinic acid (1.23 g, 10 mmol) was added to 25 mL of ethanol and stirred at room temperature until complete dissolution was observed. Magnesium ethoxide (560 mg, 4.9 mmol) was added and the slurry was heated to 80° C. Water was added drop-wise until a clear solution was obtained. The solution was filtered hot, allowed to cool to room temperature, and then kept at 4° C. overnight. The resulting white crystals were isolated by filtration, washed with ethanol, and air dried to provide 1.1 grams of crystalline MgPic in 85% yield. The $^1$H-NMR spectrum of the product (FIG. 3) was consistent with the spectrum of a metal picolinate salt. The product contained acceptable trace levels of barium and other heavy metals of less than 200 ppm of each element tested.

Example 4. Large Scale Preparation C of Magnesium Picolinate (Hydrated and Anhydrous)

Picolinic acid (12.3 g, 100 mmol) was added to 235 mL of ethanol and the reaction mixture was stirred at room temperature until complete dissolution was observed. Magnesium ethoxide (6.3 g, 55 mmol) was added and the slurry was heated to 80° C. Water was added drop-wise until a clear solution was obtained. The solution was filtered hot, allowed to cool to room temperature, and then kept at 4° C. overnight.

The resulting solid was isolated by filtration, washed with ethanol, and air dried to provide 14.5 grams of MgPic hydrate. The solid was dried at 108° C. for 2.5 hr to provide 10.8 grams of anhydrous MgPic in 81% yield. The $^1$H-NMR spectrum of the product was consistent with the spectra of MgPic obtained in Examples 2 and 3. The product contained acceptable trace levels of barium and other heavy metals of less than 200 ppm of each element tested.

Example 5. Stability of Magnesium Picolinate

Magnesium picolinate compositions of the invention were stable during storage at room temperature. The amorphous solid was not hygroscopic, as measured by weight, and showed no signs of degradation after 60 days at 40% relative humidity and 25° C. and after 30 days at 75% relative humidity and 40° C. The amorphous solid did not change color on exposure to light.

The crystalline solid was not hygroscopic, as measured by weight, and showed no signs of degradation after 60 days at 40% relative humidity and 25° C. and after 30 days at 75% relative humidity and 40° C. The crystalline solid did not change color on exposure to light.

Example 6. Serum Levels of Magnesium and Picolinic Acid

In a double-blind clinical study, 30 subjects are divided into two groups (n=15). The control group receives a supplement containing 916 mg picolinic acid and 90 mg of magnesium. The trial group receives a supplement containing 500 mg of magnesium picolinate (46 mg of magnesium and 454 mg of picolinate), or one-half the total dose of picolinate and magnesium of the control group. Serum levels of picolinic acid (ng/mL) and serum levels of magnesium (ng/mL) are measured at one hour, four hours, six hours, and eight hours. The mean serum magnesium levels for the trial group are between 80-120% of the control group at each time point. The mean serum picolinic acid levels for the trial group are between 80-120% of the control group at each time point. Thus, magnesium picolinate provides 80-120% of bioavailable magnesium, and 80-120% of bioavailable picolinic acid, relative to twice the dose of magnesium and picolinic acid alone.

Example 7. Cerebrospinal Fluid (CSF) Levels of Magnesium and Picolinic Acid

In a double-blind clinical study, 30 subjects are divided into two groups (n=15). The control group receives a supplement containing 916 mg picolinic acid and 90 mg of magnesium. The trial group receives a supplement containing 500 mg of magnesium picolinate (46 mg of magnesium and 454 mg of picolinate), or one-half the total dose of picolinate and magnesium of the control group. CSF levels of picolinic acid (ng/mL) and serum levels of magnesium (ng/mL) are measured at four hours and eight hours via spinal tap. The mean CSF magnesium levels for the trial group are between 80-120% of the control group at each time point. The mean CSF picolinic acid levels for the trial group are between 80-120% of the control group at each time point. Thus, magnesium picolinate provides 80-120% of the brain penetration of magnesium, and 80-120% of the brain penetration of picolinic acid, relative to twice the dose of magnesium and picolinic acid alone.

Example 8. Magnesium and Picolinic Acid $C_{max}$ and $T_{max}$

In a double-blind clinical study, 30 subjects are divided into two groups (n=15). The control group receives a supplement containing 916 mg picolinic acid and 90 mg of magnesium. The trial group receives a supplement containing 500 mg of magnesium picolinate (46 mg of magnesium and 454 mg of picolinate), or one-half the total dose of picolinate and magnesium of the control group. Magnesium and picolinic acid $C_{max}$ (ng/mL) and $T_{max}$ (minutes) are measured in each subject. The mean magnesium and picolinic acid $C_{max}$ for the trial group are between 80-120% of the control group at each time point. Thus, magnesium picolinate provides 80-120% of the maximum serum concentration of magnesium and picolinic acid relative to twice the dose of magnesium alone, or relative to twice the dose of picolinic acid alone. The mean magnesium and picolinic acid $T_{max}$ for the trial group are between 50-80% of the control group at each time point. Thus, magnesium picolinate delivers the maximum amount of bioavailable magnesium and picolinic acid in 50-80% less time relative to twice the dose of magnesium alone, or relative to twice the dose of picolinic acid alone.

Example 9. Magnesium and Picolinic Acid $AUC_{0 \rightarrow \infty}$

In a double-blind clinical study, 30 subjects are divided into two groups (n=15). The control group receives a supplement containing 916 mg picolinic acid and 90 mg of magnesium. The trial group receives a supplement containing 500 mg of magnesium picolinate (46 mg of magnesium and 454 mg of picolinate), or one-half the total dose of picolinate and magnesium of the control group. Magnesium and picolinic acid $AUC_{0 \rightarrow \infty}$ (ng·h/mL) are measured in each subject. The mean magnesium and picolinic acid $AUC_{0 \rightarrow \infty}$ for the trial group are between 80-120% of the control group at each time point. Thus, magnesium picolinate provides 80-120% of the maximum amount of bioavailable magnesium and picolinic acid relative to twice the dose of magnesium alone, or twice the dose of picolinic acid alone.

Example 10. Magnesium Picolinate Sustained Release

In a double-blind clinical study, 30 subjects are divided into two groups (n=15). The control group receives an enteric-coated multilayer tablet containing 916 mg picolinic acid and 90 mg of magnesium. The test group receives an enteric-coated multilayer tablet containing 500 mg of magnesium picolinate (46 mg of magnesium and 454 mg of picolinate), or one-half the total dose of picolinate and magnesium of the control group.

The $C_{max}$ (ng/mL); $T_{max}$ (minutes); and $AUC_{0-\infty}$ (ng·h/mL) for magnesium and for picolinic acid are measured in each subject. The values for $C_{max}$, $T_{max}$, and $AUC_{0-\infty}$ show a first peak in serum levels of magnesium and picolinic acid, followed by a first plateau of relatively constant blood serum levels, followed by a second peak in serum levels of magnesium and picolinic acid, followed by a second plateau of relatively constant blood serum levels. In each instance, the mean magnesium and picolinic acid $C_{max}$ and $AUC_{0-\infty}$ are between 80-120% of the control group at each time point, and the mean $T_{max}$ are between 50-80% of the control group at each time point.

Thus, the multilayer enteric-coated magnesium picolinate formulation is capable of delivering 80-120% of the maximum serum picolinic acid concentration and 80-120% of the maximum amount of bioavailable picolinic acid, in 50-80% percent of the time, relative to twice the dose of picolinic acid alone. The multilayer enteric-coated magnesium picolinate formulation is also capable of delivering 80-120% of the maximum serum magnesium concentration and 80-120% of the maximum amount of bioavailable magnesium, in 50-80% percent of the time, relative to twice the dose of magnesium alone.

Example 11. Administration of Magnesium Picolinate to Rats

Seven male Wistar rats per treatment arm (age: 8 week, weight: 180±20 g) were housed in a controlled environment with a 12:12-h light-dark cycle at 22° C. and were provided with rat chow and water ad libitum. Following a 7-day acclimatization period, animals were randomly be divided into the following groups:
1. Control (no treatment);
2. Control+MgO (500 mg elemental Mg/kg diet),
3. Control+MgPic (500 mg elemental Mg/kg diet),
4. HFD (fed with high fat diet);
5. HFD+MgO (500 mg elemental Mg/kg diet),
6. HFD+MgPic (500 mg elemental Mg/kg diet).

The MgPic administered was prepared in accordance with the methods of the inventions described herein. All treatments were administered daily as an oral supplement per day for 8 weeks. The dosage was chosen because previous studies have demonstrated the effect of this dosage in rats using methods known to those of skill in the art. The rats were subjected to several study protocols during the treatment period.

Figure 4C:
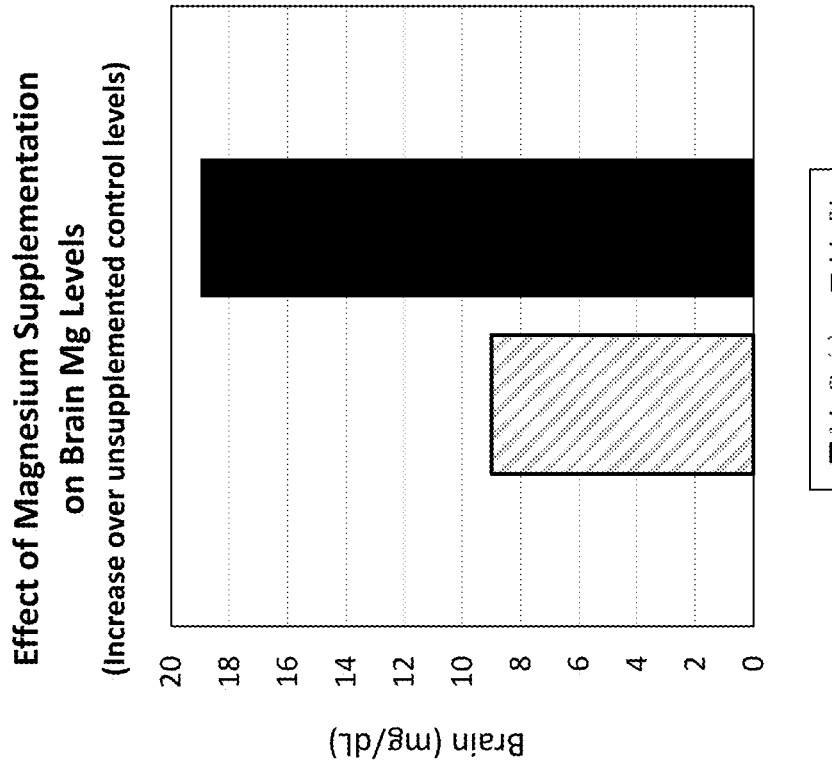
FIG. 4 shows results achieved after administration of magnesium picolinate compared to magnesium oxide.
Figure 4E:
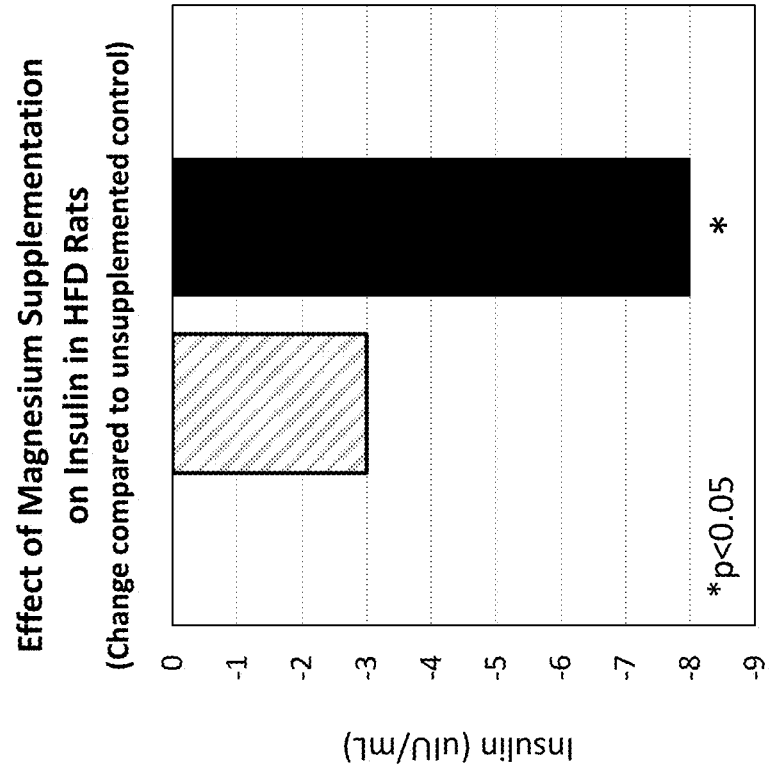
Figure 4D:
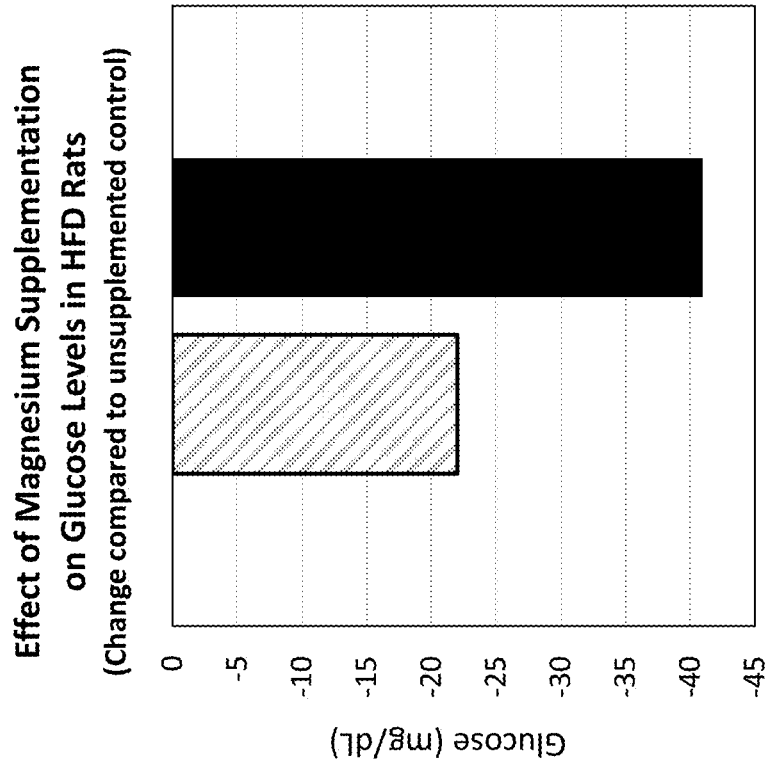
Figure 4G:
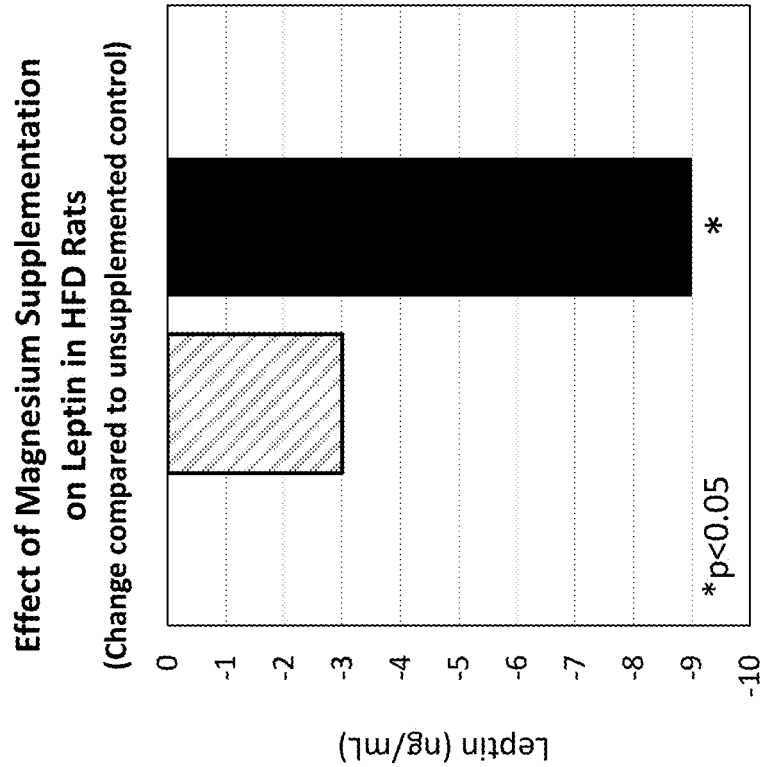
Figure 4F:
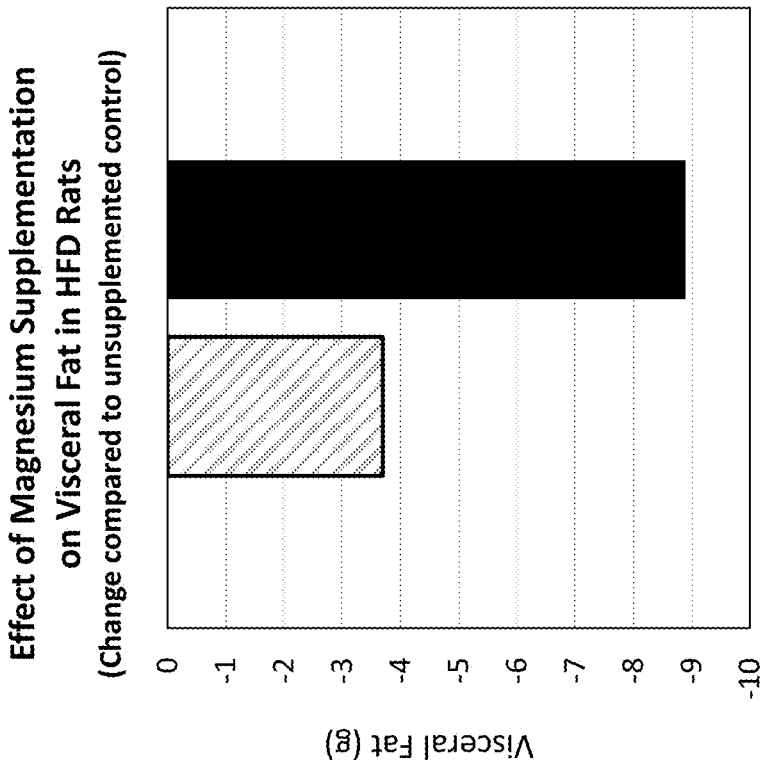

Laboratory Analyses—Following the treatment period, plasma was extracted and used for the determination of glucose, insulin, visceral fat, magnesium, and leptin concentrations, which was performed with an automatic analyzer (Samsung). Brain antioxidant enzyme catalase (CAT) and glutathione peroxidase (GSH-Px) were measured using a commercially available assay kit (Cayman Chemical, Ann Arbor, Mich., USA) according to the manufacturer's instructions. FIG. 4 shows the results of these tests and demonstrate the superior results achieved over prior art compositions and shows the comparison of administration of magnesium oxide compared to administration of magnesium picolinate (the control group consisted of rats given a standard diet). FIGS. 4A-4C show substantially improved magnesium levels that were measures in serum, liver, and brain samples, demonstrating unexpectedly improved absorption of magnesium in the rat tissues. FIGS. 4D-4E show the reduced amounts of glucose and insulin that were measured in the rats administered magnesium picolinate compared to the both the control specimens and those given magnesium oxide. FIG. 4F shows the unexpectedly improved reduction of visceral fat achieved with administration of magnesium picolinate compared to administration of magnesium oxide. FIG. 4G shows the unexpectedly superior reduction of leptin secretion achieved with administration of magnesium picolinate compared to administration of magnesium oxide.

Morris Water Maze—The water maze test was performed according to methods known to those of skill in the art. The water maze was conducted in a large circular black pool (160 cm in diameter) containing water (temperature at 24±2° C.) that had been colored with a nontoxic black dye to contrast the rat. A 12-cm-diameter black-colored round platform was placed 1.5 cm below the water surface. All of the rats were placed in the water maze room 1 h before the water maze trial daily. The rats were given a maximum time of 60 s to find the hidden platform, and they were allowed to remain on the platform for 30 s. The rats were guided to land on the platform if they failed to find the platform within 60 s. The rats were given a daily session of four trials per day for six consecutive days. The swimming pathway and latency in locating the hidden platform was recorded for each trial. On the seventh day, the time taken to reach the quadrant and the number of crossings of the target quadrant was tested with the platform removed. FIG. 5 shows the time taken for each group to reach the quadrant with the hidden platform. As can be seen by FIG. 5, administration of magnesium picolinate improved memory function both in rats fed a high fat diet and those fed the control diet. It is noted that rats fed a high fat diet experience diminished memory function. FIG. 5, therefore, presents the unexpectedly superior memory improvements (in populations with reduced memory function and populations with no diminished memory function) when subjects are administered magnesium picolinate. FIG. 6 also shows the improvements achieved when magnesium picolinate is administered to rats fed a high fat diet compared to the rats administered magnesium oxide (the "control" in FIG. 6 are rats fed a high fat diet).

Figure 7:
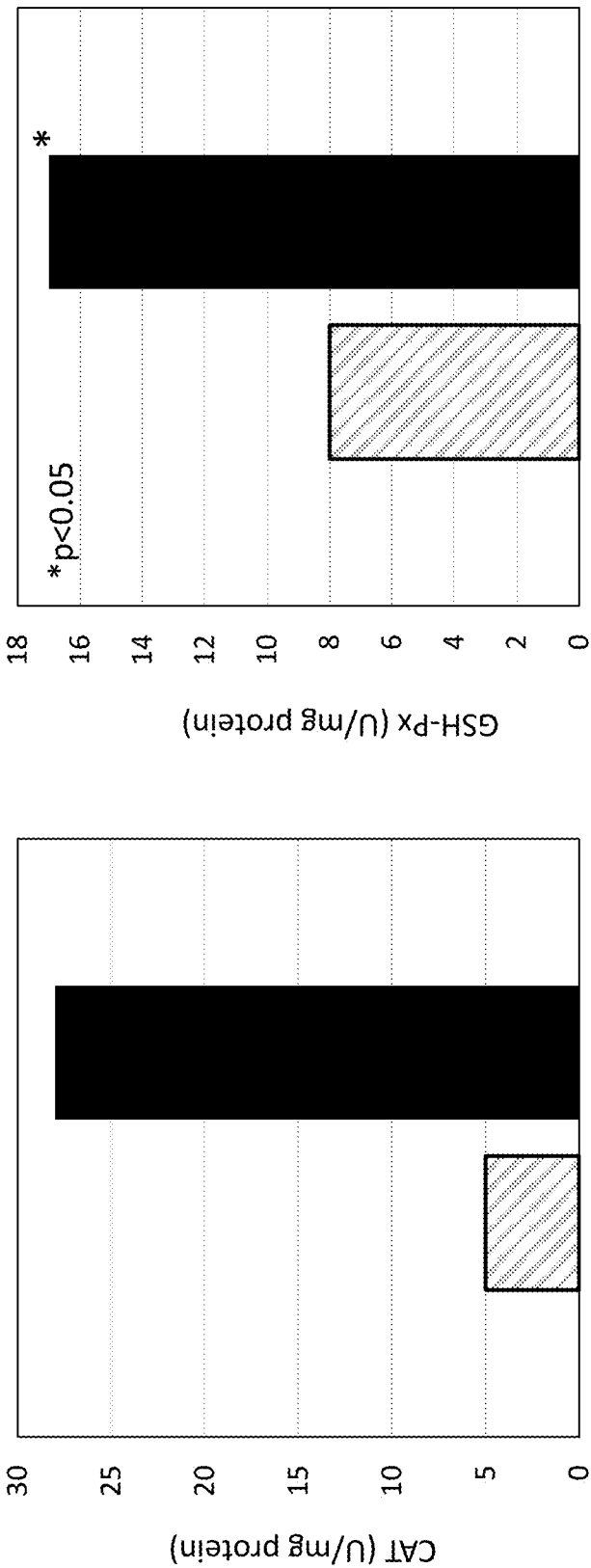
FIG. 7 shows the improved brain enzyme activity achieved by administration of magnesium picolinate.

Atomic Absorption Spectroscopy—Rat sera, liver, brains were removed and the cerebral cortex and hippocampus were dissected for analysis after the treatment period. The tissues were stored at -70° C. until analysis using atomic absorption spectroscopy (AAS). The tissues were placed in an incubator at 37° C. and allowed to achieve a constant dry weight over approximately 24 h. Thereafter, the dry tissues were weighed and digested in concentrated nitric acid in glass centrifuge tubes for 1 h at 60° C. and diluted 1:10 with distilled deionized water before analysis. All samples were processed to produce clear digests, and the total magnesium in each sample was measured by flame AAS (Perkin Elmer) using established and fully verified methods. FIG. 7A shows the superior improvements of increasing brain antioxidant enzyme (CAT) activity achieved when administering magnesium picolinate compared to magnesium oxide. FIG. 7B shows the shows the superior improvements of increasing brain antioxidant enzyme (GSH-Px) activity achieved when administering magnesium picolinate compared to magnesium oxide. The control group referenced in FIGS. 7A and 7B were fed a standard diet.

Example 12: Preparation of MgPic from Magnesium Chloride

Picolinic acid was dissolved in water at ambient temperature. Upon dissolution, 1.00 equiv. of 12.4% aq. NaOH were added with cooling over 5 min. Magnesium chloride hexahydrate (0.50 equiv.) was dissolved in water, filtered, and added with stirring over 5 min to the sodium picolinate solution at 25° C. A white precipitate formed. The suspension was heated to 70° C. for 1 hour (the mixture remained a suspension), cooled to 17° C., and filtered. The filter cake was washed with water and dried at 80 to 100° C. under vacuum. Yield approx. 93%, about 3% magnesium picolinate in the filtrate.

Example 13: Preparation of MgPic from Magnesium Oxide

Picolinic acid and magnesium oxide (0.5 equiv.) were added to water, giving a white, stirrable slurry. The slurry was heated to 95-100° C. for 3 hours, and more water was added, tripling the initial amount of water [note: the procedure was based on the preparation of a related magnesium salt using magnesium oxide, in which the initial slurry completely dissolved at 80-90° C. This dissolution did not happen with magnesium picolinate]. After cooling overnight, the mixture was filtered at 21° C., and the filter cake was rinsed with water and dried at 80 to 100° C. under vacuum. Yield approx. 89%, about 6% magnesium picolinate in the filtrate. The magnesium picolinate is soluble in ethanol/water so in the material can further be dissolved in ethanol, filtered, and precipitated with water. The sodium chloride content of the resulting product was 0.6% without any reslurries.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

When introducing elements of the present application or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present application to its fullest extent. The specific embodiments are, therefore, to be construed as merely illustrative, and not limitative of the remainder of the disclosure in any way whatsoever. While the present application has been described in some detail for purposes of clarity and understanding, one will appreciate that various changes in form and detail can be made without departing from the true scope of the application.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A composition comprising an effective amount of magnesium picolinate and a pharmaceutically acceptable vehicle, carrier, or diluent, wherein the effective amount increases magnesium levels in a subject in need thereof; wherein the composition comprises no more than 200 ppm of heavy metal cadmium, mercury, lead, nickel, arsenic, cobalt, antimony, thallium, barium, silver, selenium, copper, zinc, manganese, strontium, or a combination thereof.

2. The composition of claim 1, wherein the composition is a solid composition.

3. The composition of claim 1, wherein the composition comprises a sustained-release matrix.

4. The composition of claim 1, wherein the composition is enteric coated.

5. The composition of claim 1, wherein the composition comprises between about $9.05 \times 10^{-4}$ mg to about 905 mg of magnesium.

6. The composition of claim 1, wherein the effective amount improves metabolic function.

7. The composition of claim 1, wherein the effective amount improves memory.

8. The composition of claim 1, wherein the composition comprises less than about 200 ppm of barium.

9. The composition of claim 1, wherein the composition comprises less than about 100 ppm of barium and other heavy metals.

10. The composition of claim 1, wherein the effective amount increases brain magnesium levels.

11. The composition of claim 1, wherein the effective amount increases liver magnesium levels.

12. The composition of claim 1, wherein the effective amount increases serum magnesium levels.

13. The composition of claim 1, wherein the magnesium picolinate is safe to administer to humans without further processing.

14. The composition of claim 1, wherein the magnesium picolinate is entirely crystalline.

15. The composition of claim 1, wherein the composition further comprises sodium chloride.

\* \* \* \* \*